United States Patent [19]

Carr et al.

[11] Patent Number: 4,935,557
[45] Date of Patent: Jun. 19, 1990

[54] CONITRATION OF MIXED AROMATIC HYDROCARBONS

[75] Inventors: Richard V. Carr; Bernard A. Toseland, both of Allentown, Pa.

[73] Assignee: Air Products and Chemicals, Inc., Allentown, Pa.

[21] Appl. No.: 638,437

[22] Filed: Aug. 7, 1984

[51] Int. Cl.$^5$ ............................................. C07C 76/00
[52] U.S. Cl. ....................................... 568/934; 568/932
[58] Field of Search ............... 568/927, 932, 934, 929, 568/930; 252/182; 260/688

[56] References Cited

U.S. PATENT DOCUMENTS

| | | | |
|---|---|---|---|
| 2,256,999 | 9/1941 | Castner | 260/645 |
| 2,370,558 | 2/1945 | Mares | 260/645 |
| 2,739,174 | 3/1956 | Ross | 260/645 |
| 2,773,911 | 12/1956 | Dubois et al. | 260/645 |
| 2,849,497 | 8/1958 | Buchanan | 260/645 |
| 2,934,571 | 4/1960 | Bonetti | 260/645 |
| 3,092,671 | 6/1963 | Humphrey et al. | 260/645 |
| 3,434,802 | 3/1969 | Toischer et al. | 23/260 |
| 3,780,116 | 12/1973 | Sahgal | 260/645 |
| 3,928,395 | 12/1975 | Seha et al. | 568/929 |
| 4,005,102 | 1/1977 | Cook et al. | 568/930 |
| 4,021,498 | 5/1977 | Alexanderson et al. | 260/645 |
| 4,036,838 | 7/1977 | Vogel et al. | 568/930 |
| 4,112,005 | 9/1978 | Thiem et al. | 260/645 |
| 4,185,006 | 1/1980 | Rasberger et al. | 260/45.8 |
| 4,185,036 | 1/1980 | Cossaboon | 260/580 |
| 4,224,249 | 9/1980 | Kunz et al. | 260/580 |
| 4,495,372 | 1/1985 | Feiccabrino | 568/929 |

*Primary Examiner*—John F. Terapane
*Assistant Examiner*—Valerie D. Fee
*Attorney, Agent, or Firm*—Russell L. Brewer; James C. Simmons; William F. Marsh

[57] ABSTRACT

This invention relates to the preparation of a mixture of nitroaromatic compositions, particularly a mixture of mononitrobenzene and dinitrotoluene. The conitration of a mixture of aromatic hydrocarbons is accomplished by contacting the mixture of hydrocarbons with nitric acid, in the absence of sulfuric acid, at temperatures of from about 40° to 70° C. By the use of nitric acid alone, one avoids the heterogeneous nitration associated with the use of sulfuric acid and thereby one can effectively produce a reaction mixture containing mononitrobenzene and dinitrotoluene.

2 Claims, No Drawings

CONITRATION OF MIXED AROMATIC HYDROCARBONS

TECHNICAL FIELD

This invention pertains to the preparation of mixed nitroaromatic compositions, particularly mixed nitration products of benzene and toluene or xylene.

BACKGROUND OF THE INVENTION

Nitroaromatic compositions have been widely used as intermediates in the chemical industry and are suited for producing a variety of industrial chemicals. Typically the nitroaromatic compositions are hydrogenated to form the aromatic amine which then can be used in preparing dyestuffs, or as an intermediate in the urethane industry. Examples of widely used nitroaromatics which are subsequently hydrogenated to the amine include nitrobenzene, dinitrotoluene, and dinitroxylene. These compositions when hydrogenated form aniline, toluenediamine, and xylenediamine, respectively. The former has wide utility for the dyestuff industry while the latter diamines are used as intermediates in the production of diisocyanates for urethane manufacture.

Numerous processes have been developed for effecting nitration of aromatic hydrocarbons; some have focused on the synthesis of mononitroaromatics while others are focused on the production of dinitro or trinitro aromatic compositions. Nitration of aromatic compositions have typically been done by the mixed acid technique, i.e. a mixture of nitric acid and sulfuric acid, although nitration of aromatics has also been affected utilizing nitric acid alone or mixtures of nitrogen oxides and sulfuric acid. Representative patents illustrating some of the nitration techniques are as follows:

U.S. Pat. Nos. 2,362,743, 2,739,174 and 3,780,116 disclose processes for the nitration of aromatic hydrocarbons using nitric acid as the sole nitrating medium. The '743 patent uses a two-stage nitration process to form dinitrotoluene in the first stage, toluene is nitrated with 60–75% nitric acid at temperatures about 75°–80° C. and then dinitrated with 90–100% nitric acid at the same temperature. In the '174 patent benzene, toluene, and xylene were nitrated using 70% nitric acid at temperatures of from about 110°–120° C. In the process, a liquid reaction mixture comprising water, nitric acid and nitrated hydrocarbon was withdrawn from the reactor and the nitric acid separated from the water nitrated hydrocarbon azeotrope via distillation. The '116 patent used approximately 40% nitric acid as the nitrating medium for benzene and toluene and the process involved bubbling hydrocarbon vapor through the nitric acid medium at temperatures of from about 50°–100° C. A nitrobenzene-nitric acid mixture is withdrawn from the reactor and the mixture separated by decavitation. Nitric acid and unreacted benzene and water are removed as vapor with the benzene being separated and returned.

By and large the technique for nitrating aromatic hydrocarbons such as benzene, toluene, zylene, napthalene, anthraquinone has been the mixed acid technique. U.S. Pat. Nos. 2,256,999; 2,370,558; 2,773,911; 2,849,497; 3,434,802; 4,021,498; and 4,112,005 disclose variations in the mixed acid technique for producing nitroaromatic compositions and particularly, mono and dinitroaromatic compositions. The mixed acid technique is preferred in the manufacture of nitroaromatics since the concentration of the nitronium ion, which is the nitrating agent, is much lower in nitric acid alone than in the mixed acid. In the mononitration of aromatics, the aromatic hydrocarbons are contacted with a nitric acid/sulfuric acid mixture, the nitric acid concentration typically being about 20–70% by volume or more dilute than in dinitration reaction. The sulfuric acid typically used in 80–98% concentration.

The '005 patent mentioned above discloses preparing the mononitroaromatic compounds by nitrating a reactive aromatic compound in the absence of sulfuric acid until mononitration is complete, the nitration being carried out at 40–68% by weight nitric acid.

Dinitroaromatics, e.g. dinitroxylene and particularly dinitrotoluene have been typically produced by using highly concentrated nitric acid compositions or the mixed acid technique and U.S. Pat. Nos. 2,362,743; 2,934,571; and 3,092,671 are representative. The '743 patent effects dinitration of toluene in the absence of sulfuric acid. The mononitration is carried out with 70% nitric acid, while the dinitration is carried out using 98% nitric acid at temperatures of about 70°–80° C. High mole ratios of acid. e.g. 2–5:1 moles nitric acid per mole hydrocarbon, are required. The '571 patent discloses the nitration of various aromatics such as benzene. nitrobenzene, halogen-substituted benzenes, and so forth by the mixed acid technique. In that process a mixture of fuming nitric acid and fuming sulfuric acid are reacted with the aromatic hydrocarbon at temperatures of 50°–60° C.

Commercially, the nitration of toluene to form dinitrotoluene is done in a two-step process Wherein mononitrotoluene is formed in a first stage, the water of reaction and spent acid being removed from the mononitrobenzene reaction product and then the mononitrobenzene charged to the dinitrator for subsequent nitration.

The hydrogenation of nitroaromatics to the amine, e.g. nitrobenzene to aniline and dinitrotoluene to toluenediamine, usually has been carried out by effecting the hydrogenation in aqueous phase over a hydrogenation/dehydrogenation catalyst such as Raney nickel. Normally in the hydrogenation process, the nitrated product is purified and removed of acidic material and alkaline material which act as catalyst poisons in the hydrogenation reaction. U.S. Pat. No. 4,224,249 discloses such a process for this hydrogenation.

Recently it has been reported (U.S. Pat. No. 4,185,036) that mixed nitroaromatic compositions can be hydrogenated under appropriate conditions to form aromatic amines with less by-product tars at higher rates and higher yields than are achieved with prior art hydrogenation processes. More particularly, the patent discloses that a mixture of aromatic compounds can be selectively hydrogenated to the amine, the mixture containing at least 25% of a mononitrononaminoaromatic compound and at least 25% of a dinitro or a mononitro-amino compound. Examples of reactants which are suited for the selective cohydrogenation include o-nitrotoluene, o-nitroaniline, mononitrotoluene, dinitrobenzene, dinitrotoluene and other nitro aromatics.

In view of the ability to selectively hydrogenate mixed aromatic compounds while reducing the amount of tar formation during the hydrogenation of such compounds, a need was created for feeds of mixed nitroaromatic compositions. The need was originally satisfied by mixing a purified mononitronon-amino compound with a purified dinitro compound or a nitroamino aromatic and the hydrogenation effected of that mixture. Although this process is well-suited to the creation of mixed nitroaromatic compounds, there were problems associated in the preparation of the purified nitroaromatics due to the reaction conditions and separation techniques.

SUMMARY OF THE INVENTION

This invention pertains to the manufacture of a mixture comprising a mononitro aromatic compound and a dinitro aromatic compound, optionally including other nitro aromatics, which can be selectively cohydrogenated to form the corresponding aromatic amine. In a preferred embodiment, the nitro aromatic composition comprises a mixture of mononitrobenzene and dinitrotoluene. The process involves the reaction of a feed mixture comprising benzene and toluene with nitric acid under conditions suited for nitration. Typically, the nitric acid concentration is from 88 to 95% by weight at the steady state and the reaction temperature is from 40° to 70° C. The reaction time is sufficient to effect mononitration of the benzene but insufficient for effecting substantial dinitration of the benzene in the feed mixture.

Many advantages are associated with the process of this invention, and these advantages include:

the ability to utilize refinery streams comprising benzene and toluene, optionally with small amounts of xylene, without prior separation to form a suitable feedstock for nitration:

an ability to selectively nitrate a feed mixture to form a nitroaromatic mixture consisting primarily of mononitrobenzene and dinitrotoluene as the nitrated benzene and toluene products;

an ability to selectively form mononitrobenzene and dinitrotoluene in combination with each other for further hydrogenation without a plurality of separation stages involving the separation of unstable nitroaromatic compositions; and an ability to reduce the amount of process steps necessary to produce aromatic amine intermediates without numerous separation stages prior to the generation of such aromatic amine intermediates.

DETAILED DESCRIPTION OF THE INVENTION

This invention is particularly adapted to the nitration of hydrocarbon feedstocks consisting primarily of benzene and toluene with optional amounts of other aromatic hydrocarbons, e.g. xylene. Typically, these feedstocks comprise from about 20 to 80 wt % benzene, 20 to 80% toluene and the balance consisting of xylene or other hydrocarbons such as napthalene or non-nitratable hydrocarbon. Although the nitration of a feed mixture of benzene and toluene can be broadly reacted where the benzene is present in a proportion of from 5 to 95% by weight, preferred reaction systems comprise from about 20 to 80% benzene and 20 to 80% toluene so that desired levels of both mononitrobenzene and dinitrotoluene can be produced for cohydrogenation.

Nitration of the aromatic hydrocarbon stream is effected by utilizing essentially concentrated nitric acid alone as the nitrating agent. The presence to sulfuric acid or other dehydration agent in an amount in excess of about 20% by weight, such as would be encountered in the mixed acid technique, interferes with the selectivity of the nitration to mononitrobenzene and dinitrotoluene. For example, the presence of sulphuric acid will lead to higher formations of mononitrotoluene and dinitrobenzene. For these reasons, it is preferred to use a nitration medium comprising only nitric acid as the nitrating medium.

Nitric acid concentrations for effecting nitration should be from about 82 to 95% by weight and preferably 86 to 92%. When the concentration of nitric acid falls below about 82%, then nitration conditions typically have to be more rigorous in terms of temperature or in terms of increased reaction time. The use of these conditions often leads to increased by-product formation, e.g. dinitrobenzene or a product mix of mono and dinitrotoluene. On the other hand, as the concentration of nitric acid is increased above 95%, e.g. as in the use of fuming nitric acid, no substantial advantages appear to be achieved.

The temperature and reaction time for effecting nitration of the aromatic hydrocarbon is adjusted to accommodate the manufacture of mononitrobenzene and dinitrotoluene in high selectivity without the formation of significant amounts of by-products. Typically, temperatures are from 40° to 70° C. and reaction times of from 2 to 8 minutes are utilized. As previously mentioned as the temperature is increased, there is a tendency to produce undesirable by-products. e.g. dinitrobenzene, and as the temperature is reduced, long reaction times may be required which also permit the formation of increased levels of dinitrobenzene.

Conventional techniques for removing water from the reaction mixture can be utilized in the practice of this invention. These techniques can invoice a process wherein side streams are removed from the reactor, the reaction product then separated into an organic and aqueous phase, and the aqueous phase removed with the organic phase being recycled to the reactor for further reaction. This particular technique permits the nitration to be carried out either in a continuous or batch mode. After the nitration is completed, the reaction product is purified by separating the aqueous phase, including spent nitric acid, from the organic phase and stripped under moderate temperatures to remove volatiles. Optionally, the organic phase can be treated with aqueous alkaline solutions, such as dilute caustic soda or sodium carbonate, to remove undesirable hydrocarbons such as nitrocresols and nitrophenols. However, since it has been observed that there is substantially no tar or undesirable nitrobody formation by the practice of this nitration process, the purification step involving the removal of nitrocresols and other nitrophenolic material may be omitted.

The following examples are provided to illustrate various embodiments of the invention and are not intended to restrict the scope thereof. All parts are parts by weight and all percentages are expressed as weight percentages unless specifically recited otherwise.

EXAMPLE 1

Nitration (Run 1) of a hydrocarbon mixture containing 124.8 grams (1.6 mole) of benzene and 147.2 grams (1.6 mole) of toluene was effected by first charging 50 milliliters of 90 wt % nitric acid into a stirred, glass tank reactor equipped with a stainless steel cooling coil. The benzene-toluene mixture was introduced into the reactor at a rate of 2.3 grams per minute, and the 90% by weight nitric acid being introduced at the rate of 12 grams per minute. After reaction was experienced (by evidence of a slight temperature rise and exothermic conditions), a nitroaromatic-nitric acid-water mixture was continually withdrawn from the apparatus at about the same rate that the benzene-toluene mixture and nitric acid were introduced. The reaction temperature was maintained at 40° C. by removing heat via the stainless steel cooling coils. As the reaction product was removed from the reactor it was quenched by contact with ice. The product then was purified by removing water and spent acid and the organic phase then analyzed by gas chromatographic techniques. Conversion was estimated to be about 100% based upon aromatic compound A similar run to Run 1, i.e., Run 2, was made at 70° C.

The above procedure was repeated as Run 2, except that the temperature of the reaction was maintained at 70° C. as opposed to the 40° C. Table 1 provides gas chromatograph results for both reactions carried out under the above recited conditions. Conversion was estimated to be about 100% based upon hydrocarbon conversion.

TABLE 1

| GC Analysis of Benzene-Toluene Nitration with Nitric Acid | | |
|---|---|---|
| Compound | Run 1 T = 40° C. Mole % | Run 2 T = 70° C. Mole % |
| Benzene | 0 | 0 |
| Toluene | 0 | 0 |
| Nitrobenzene | 42.75 | 40.76 |
| Nitrotoluenes | 1.58 | 0.55 |
| Dinitrobenzene | 1.59 | 5.22 |
| Dinitrotoluene | 54.09 | 53.47 |

It can readily be noted from the table at both the 40° C. and 70° C. temperatures that there is high selectivity to a reaction product consisting of mononitrobenzene and dinitrotoluene, particularly at the 40° C. level. Essentially less than 3% of the nitrated product is converted to mononitrotoluene or dinitrobenzene. On the other hand, as the temperature is increased to 70° C. there is a slight increase in the amount of dinitrobenzene produced. However, since this is a dinitrated product, it can be used as a chain extender in other applications where aromatic diamines are suited. It does not present a substantial problem with respect to separation.

EXAMPLE 2

A series of nitration runs using benzene, toluene and xylene as the hydrocarbon feedstock were carried out in accordance with the general technique of Example 1. Numerous process conditions were varied in terms of feed composition, temperature, residence time, and nitration medium in order to observe the effect of the variation in product distribution as a function of these process variables. Table 2 below sets forth the general reaction and process conditions, as well as the product distribution.

TABLE 2

| | | | | | BTX Nitration with Nitric Acid | | | | | | |
|---|---|---|---|---|---|---|---|---|---|---|---|
| | T | Res. Time | HNO$_3$* | Acid/Org | | | Mole % | | | | |
| Run # | (°C.) | (min) | (wt %) | (g/g) | MNB | DNB | MNT | DNT | DNX | TNX | |
| 1 | 50 | 6.6 | 92.9 | 7.0/1.0 | 29.3 | 0.18 | 2.2 | 59.5 | 8.74 | — | Feed Composition |
| 2 | 75 | 6.6 | 92.9 | 7.0/1.0 | 26.6 | 0.85 | 0.60 | 63.3 | 8.21 | 0.5 | 28 mole % benzene |
| 3 | 50 | 6.7 | 93.1 | 6.0/1.0 | 28.3 | 0.12 | 10.4 | 52.2 | 8.98 | — | 63 mole % toluene |
| 4 | 75 | 6.7 | 92.1 | 6.0/1.0 | 27.6 | 0.40 | 3.5 | 59.9 | 8.61 | — | 9 mole % xylene |

| | | | Conitration of Benzene/Nitrotoluene with Mixed Acid | | | | | |
|---|---|---|---|---|---|---|---|---|
| Run # | Benzene nitrotoluene mole ratio | H$_2$SO$_4$ mole % | HNO$_3$ wt % at steady state | Res. time (min) | T (°C.) | MNB (mole %) | DNB (mole %) | MNT (mole %) | DNT (mole %) |
| 5 | 1:1 | 49.3 | 3.13 | 8.75 | 70 | 51.13 | 0.36 | 22.24 | 26.18 |
| 6 | 1:1 | 53.6 | 3.38 | 8.75 | 70 | 43.42 | 7.13 | 1.69 | 47.76 |

*On an organic free basis - at the steady state in the CSTR.

What is claimed is:

1. In a process for producing a mixture of nitroaromatic compositions suited for cohydrogenation containing at least 25% of a mononitrononaminoaromatic compound and at least 25% of a dinitroaromatic compound, the improvement for producing such mixture which comprises:

utilizing a nitration feedstock consisting essentially of 80-20% by weight benzene and 80-20% by weight toluene;

contacting said nitration feedstock with a nitration medium consisting essentially of nitric acid and the concentration of said nitric acid is from 90-98% by weight;

maintaining a temperature from 40°-70° C. during acid contacting for a time sufficient to form dinitrotoluene and mononitrobenzene, but insufficient for forming dinitrobenzene in an amount in excess of 3% by weight of the reaction product consisting of a mixture of nitroaromatic compositions.

2. The process of claim 1 wherein the reaction time is from 2 to 8 minutes.

* * * * *